United States Patent

[19] Okoshi

[11] Patent Number: 5,959,140
[45] Date of Patent: Sep. 28, 1999

[54] PROCESS FOR PRODUCING AROMATIC CARBOXYLIC ACID

[75] Inventor: Fumio Okoshi, Okayama-ken, Japan

[73] Assignees: Mitsubishi Gas Chemical Company, Inc., Tokyo, Japan; Toyo Boseki Kabushiki Kaisha, Osaka, Japan; Mizushima Aroma Company, Ltd., Kurashiki, Japan

[21] Appl. No.: 09/162,058

[22] Filed: Sep. 28, 1998

[30] Foreign Application Priority Data

Oct. 3, 1997 [JP] Japan .................................. 9-271321

[51] Int. Cl.⁶ .................................................... C07C 51/10
[52] U.S. Cl. ............................................................. 562/414
[58] Field of Search ............................................. 562/414

[56] References Cited

U.S. PATENT DOCUMENTS 2,175,879  10/1939  Coutour ..................................... 202/42
4,204,915   5/1980  Kurata et al. ............................. 203/2

OTHER PUBLICATIONS

Chem Abstracts 1979:491377, Duelsen et al.

*Primary Examiner*—Samuel Barts
*Attorney, Agent, or Firm*—Frishauf, Holtz, Goodman, Langer & Chick, P.C.

[57] ABSTRACT

There is disclosed a process for producing an aromatic carboxylic acid (e.g.iso-or-tere-phthalic acid) by liquid-phase oxidation of an alkyl-group-substituted aromatic compound (e.g. p-or-m-xylene) in acetic acid which comprises dehydrating water-containing acetic acid by azeotropic distillation in an azeotropic distillation dehydration tower to recycle the dehydrated acetic acid as the solvent, and suppressing the concentration of the alkyl-group-substituted aromatic compound in the entrainer (e.g. n-butyl acetate) which is fed at the top portion of the above tower, to at most 10% by weight by removing the above aromatic compound. The process makes it possible to proceed with efficient dehydration of water-containing acetic acid for a long period of time by preventing the separation efficiency between acetic acid and an azeotropic component from being deteriorated by the alkyl-group-substituted aromatic compound remaining in the azeotropic component.

10 Claims, 1 Drawing Sheet

PROCESS FOR PRODUCING AROMATIC CARBOXYLIC ACID

BACKGROUND OF THE INVENTION

1. Field of the Invention

The present invention relates to a process for producing an aromatic carboxylic acid by a liquid-phase oxidation of an alkyl-group-substituted aromatic compound. More particularly, the present invention is concerned with the recovery of acetic acid which is used as a solvent in the aforesaid liquid-phase oxidation in said process.

2. Description of the Related Arts

A general process for producing an aromatic carboxylic acid such as terephthalic acid or isophthalic acid is a process in which an alkyl-group-substituted aromatic compound as the starting raw material is subjected to a liquid-phase oxidation by the use of molecular oxygen gas in acetic acid as a solvent in the presence of a catalyst. Since the acetic acid used as a solvent in the aforesaid process is diluted with water formed in the oxidation reaction, it is necessary to separate said water and return the acetic acid to the oxidation reactor for recycling through a distillation dehydration tower.

That is to say, said process obliges the acetic acid to be dehydrated into concentrated acetic acid in a dehydration tower for the purpose of reuse as the solvent, since water formed in the liquid-phase oxidation reaction is mixed in the water-containing acetic acid, for example, which is obtained by evaporating the reaction mother liquor produced by separating an aromatic carboxylic acid from the oxidation reaction product in the form of a slurry, or which is obtained by cooling condensing the exhaust gas coming out from an oxidation reactor.

The foregoing dehydration tower is charged with the water-containing acetic acid at an intermediate stage thereof, distills away water at the top portion, and discharges concentrated acetic acid at the bottom portion. However, since the water distilled away at the top portion of the tower is discharged to the outside of the system, the concentration of the acetic acid contained in the discharged water must be suppressed to a minimum level. In order to respond to such a demand, it is obliged to construct a dehydration tower having a large number of distillation trays and also to consume a great deal of energy.

In order to suppress at least part of the factors of increasing these costs involved in the recovery of acetic acid, there is proposed an azeotropic dehydration process which employs n-butyl acetate or the like as an azeotropic agent, for example, there is disclosed a method for separating acetic acid from water through azeotropic distillation by the use of an entrainer (azeotropic agent) in Japanese Patent Publication No. 31091/1986 (Sho-61).

In the meanwhile, a long-term continuous operation was carried out by the present inventors for an azeotropic dehydration pilot plant of acetic acid by using n-butyl acetate as an azeotropic agent, and using, as a starting raw material, the mixture of acetic acid and water containing oxidation reaction water which mixture was formed from commercially operated plants for producing terephthalic acid and isophthalic acid. As a result, there was observed a phenomenon such that the separation efficiency of acetic acid from azeotropic components (n-butyl acetate/water) gradually decreases with the lapse of time and day from the start of running the azeotropic dehydration pilot plant (refer to Comparative Examples 1&2).

SUMMARY OF THE INVENTION

It is a general object of the invention to provide a process for producing an aromatic carboxylic acid by the liquid-phase oxidation of an alkyl-group-substituted aromatic compound through the azeotropic dehydration of water-containing acetic acid, said process being characterized in that the acetic acid is efficiently dehydrated by preventing the deterioration of the separation efficiency between acetic acid and azeotropic components.

As the result of pursuit of the cause for the above-mentioned phenomenon carried out by the present inventors, it has been ascertained that a slight amount of unreacted p-xylene was contained in the reflux liquid in commercially operated oxidation reactors, and that the p-xylene was gradually accumulated in n-butyl acetate as the azeotropic agent with the lapse of time and day from the start of running the azeotropic dehydration pilot plant, thus resulting in a decrease in the separation efficiency. At the same time, it was found that it is made possible to prevent the deterioration of the separation efficiency between acetic acid and azeotropic components and also to efficiently perform the dehydration, by removing p-xylene from the entrainer through distillation. Further it was found that the same working effect as the foregoing can be exerted in the production of isophthalic acid from m-xylene as the starting raw material. The present invention has been accomplished by the findings and information as described hereinbefore.

Specifically the present invention provides a process for producing an aromatic carboxylic acid which comprises subjecting an alkyl-group-substituted aromatic compound to liquid-phase oxidation with molecular oxygen in acetic acid as a solvent in the presence of a catalyst; producing water-containing acetic acid by cooling condensing an exhaust gas from an oxidation reactor, or by evaporating the oxidation reaction mother liquor after separating the aromatic carboxylic acid from the oxidation reaction liquid; and dehydrating the resultant water-containing acetic acid by means of azeotropic distillation in an azeotropic distillation dehydration tower by using an entrainer to recycle the dehydrated acetic acid as the solvent, said process being performed so as to suppress the concentration of the alkyl-group-substituted aromatic compound in the entrainer which is fed at the top portion of said tower, to at most 10% by weight.

Figure 1:
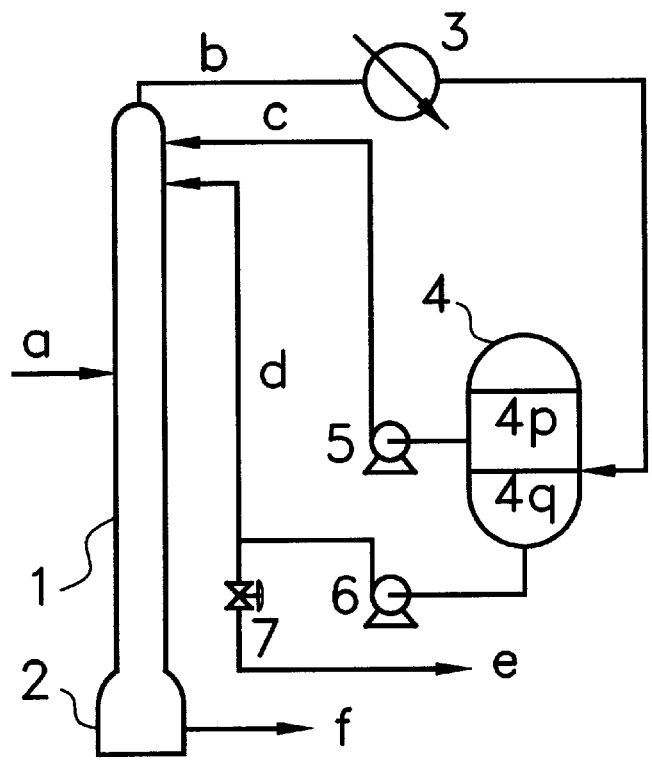
FIG. 1 is a process flow diagram showing a dehydration apparatus for water-containing acetic acid to be employed in comparative examples and reference examples.

1: azeotropic distillation dehydration tower
2: reboiler for azeotropic distillation dehydration tower
3: condenser for azeotropic distillation dehydration tower
4: decanter for azeotropic distillation dehydration tower
9: entrainer-rectifying tower
10: reboiler for entrainer-rectifying tower
11: condenser for entrainer-rectifying tower
a: water-containing acetic acid
4$p$: entrainer layer (upper layer)
4$q$: water layer (lower layer)
e: separated water
f: acetic acid k: alkyl-group-substituted aromatic compound containing entrainer

DESCRIPTION OF THE PREFERRED EMBODIMENTS p-Xylene and m-xylene are each preferably employed as an alkyl-group-substituted aromatic compound to be used as a starting material for oxidation in the present invention. As the corresponding aromatic carboxylic acid, terephthalic acid and isophthalic acid are preferably produced.

In this case, acetic acid is used as an oxidation reaction solvent for producing an aromatic carboxylic acid by the liquid-phase oxidation of an alkyl-group-substituted aromatic compound. There is used as a catalyst, a transition metal compound such as manganese, cobalt, iron, chromium or nickel. A promoter such as a bromine compound is used as the case may be. In the case of a bromine base catalyst being out of use, a promoter such as acetaldehyde or methyl ethyl ketone is used for a cobalt catalyst.

There is used molecular oxygen, usually air as an oxidizing agent. It is possible to use air which is enhanced in oxygen concentration by mixing oxygen gas or inversely, air which is decreased in oxygen concentration by mixing an inert gas such as nitrogen gas.

There is usually adopted a reaction temperature of the liquid-phase oxidation in the range of 120 to 220° C. The reaction pressure needs only to be in the range capable of maintaining the liquid phase of acetic acid as the solvent. In the case of an oxidation reaction system without the use of a bromine base catalyst, the reaction temperature thereof is usually not higher than 160° C.

The oxidation reaction heat is removed usually by flash evaporation of the water-containing acetic acid as the reaction solvent. That is to say, large amounts of evaporated acetic acid and water, which are contained in an exhaust gas discharged from the oxidation reactor, are condensed by cooling into liquid in a condenser, refluxed in part to the oxidation reactor, and discharged in part to the outside of the system for the purpose of removing the water formed by the oxidation reaction. The discharged liquid, which is composed mainly of the mixture of acetic acid and water, contains slight amounts of oxidation reaction byproducts having a low boiling point, unreacted alkyl-group-substituted aromatic compounds and the like. The water-containing acetic acid obtained by cooling condensing the exhaust gas is fed in the dehydration tower.

At least one unit of reactor is employed for the liquid-phase oxidation reaction of an alkyl-group-substituted aromatic compound. The reaction liquid after the completion of the oxidation reaction may be transferred to one or two or more continuous crystallizers that are consecutively reduced in working pressure, where the reaction liquid is cooled by flash evaporation action to temperatures corresponding to respective pressures. The aromatic carboxylic acid thus formed is crystallized in most part into a slurry solution.

The resultant slurry solution is separated into the aromatic carboxylic acid in the form of a cake and the oxidation reaction mother liquor, by a rotary vacuum filtration method, a centrifugal separation method or an other suitable separation method.

The aromatic carboxylic acid in the form of cake thus separated is washed at need with acetic acid or water, and the solvent stuck thereto is removed with a dryer to produce the objective aromatic carboxylic acid.

Part of the oxidation reaction mother liquor thus separated is recycled as such or via such a treatment as oxidation or reduction. The remainder thereof is usually evaporated by the use of an evaporator, a film evaporator or the like to remove water and the byproduct that are formed by the oxidation reaction, and is separated into an evaporation residue and vapor composed mainly of acetic acid, water and slight amounts of unreacted alkyl-group-substituted aromatic compound and low-boiling-point reaction products. The separated vapor or the condensate thereof is sent to the dehydration tower, while the evaporation residue is passed through various treatment steps to recover the effective catalyst ingredients, and thereafter unnecessary components are discarded to the outside of the system.

As mentioned hereinbefore, the liquid fed to the azeotropic dehydration tower (hereinafter abbreviated to "dehydration tower") which recovers acetic acid solvent from oxidation reaction condensate or oxidation reaction mother liquor, comprises acetic acid and water as main components and slight amounts of the unreacted alkyl-group-substituted aromatic compound and low-boiling-point oxidation reaction products.

The feed liquid (water-containing acetic acid as the starting material) is supplied to the dehydration tower at an intermediate stage thereof, and there is withdrawn at the bottom thereof, water-containing acetic acid concetrated by dehydration to the extent that said water-containing acetic acid is usable for the oxidation reaction, while the entrainer is fed in the dehydration tower at the top portion thereof. The azeotropic mixture of the entrainer and water is distilled away at the top thereof. The distillate usually contains an extremely low concentration of acetic acid.

As the entrainer for use in the dehydration tower according to the present invention, there is employed any of azeotropic agents which have heretofore been used in a mixed solution of acetic acid and water. Examples of such entrainers include compounds which are capable of forming an azeotropic mixture at an azeotropic point in the range of 100 to 150° C., and specifically esters such as butyl formate, amyl formate, n-butyl acetate, isobutyl acetate, allyl acetate, n-propyl propionate, iso-propyl propionate, n-butyl propionate and iso-butyl propionate; ethers such as dichloromethyl ether and ethylisoamyl ether; halogenated hydrocarbons such as amyl chloride and ethylene dichloride; ketones such as acetone chloride and ethyl propyl ketone; and aromatic hydrocarbons such as toluene. Of these, the esters are preferable, and n-butyl acetate is particularly preferable.

The azeotropic mixture which is distilled away at the top of the dehydration tower is cooled and condensed in a condenser, and the resultant condensate is separated into the entrainer and water by the use of an appropriate separator such as a decanter. Part of the separated water is discharged to the outside of the reaction system, while another part of the water is refluxed to top portion of the dehydration tower. In this case, the reflux ratio (flow rate of refluxed water/flow rate of discharged water) is set usually on about 0.1 to 3.

It is indispensable in the present invention that the concentration of alkyl-group-substituted aromatic compounds in the entrainer to be fed to the top portion of the dehydration tower be suppressed to at most 10% by weight. For the sake thereof in the present invention, part of the separated entrainer is introduced in an entrainer-rectifying tower (hereinafter abbreviated to "rectifying tower"), where most of the entrainer is recovered through the top portion, and the alkyl-group-substituted aromatic compounds containing some amount of the entrainer are taken out through the bottom thereof.

A practical rectifying tower may be operated by a batchwise system in which the concentration of alkyl-groupsubstituted aromatic compounds in the entrainer inside the decanter is monitored, and when said concentration rises to a critical level, the rectifying tower is put into operation. However, a continuous system is more simple and more convenient.

In the case of a continuous system, the entrainer which is taken out from the decanter is fed in the rectifying tower at an intermediate stage thereof. The vapor which is distilled away through the top thereof is cooled in a condenser into a condensate composed principally of the entrainer, part of which is refluxed to the top portion of the rectifying tower, the remainder being returned to the decanter. The alkyl-group-substituted aromatic compound containing some amount of the entrainer is discharged through the bottom thereof.

Although depending upon the performance and operation system of the dehydration tower and the rectifying tower, the entrainer-containing alkyl-group-substituted aromatic compound is usually in a slight amount, and accordingly is disposed of in an incinerator.

The structure and practical operation method of the rectifying tower are not specifically limited.

In the following, the present invention will be described in more detail with reference to comparative examples and working examples, which however shall not limit the present invention thereto. All part, parts and % are based on weight unless otherwise denoted.

COMPARATIVE EXAMPLE 1

By the use of the apparatus as illustrated in FIG. 1, dehydration was performed of a reflux liquid of oxidation reaction in a commercially operated production plant for terephthalic acid, said reflux liquid (hereinafter referred to as "water-containing acetic acid") comprising about 60% of acetic acid and the balance mainly of water.

There was used as a dehydration tower 1, an Oldershow type glass-made fractionating tower equipped with 42 perforated plates, and a reboiler 2 was charged in advance, with water-containing acetic acid. A decanter 4 was charged with n-butyl acetate and water so as to form n-butyl acetate layer 4p (upper layer) and water layer 4q (lower layer). Then the reboiler was heated for steaming into the tower. The resultant vapor was passed through a top line b, cooled in a condenser 3, and the condensate thus formed was introduced in a decanter 4. Then by operating a pump 5, the n-butyl acetate of the upper layer 4p was fed at the top of the tower through a line c, and subsequently by operating a pump 6, the water of the lower layer 4q was fed at the top of the tower through a line d. After several hours of continuous operation under the aforesaid conditions, the water-containing acetic acid was fed in the tower through a line a, and simultaneously therewith a valve 7 was opened to discharge part of the water discharged by the pump 6 to the outside of the system through a line e. The concentrated acetic acid which had been accumulated in the reboiler 2 was consecutively discharged to the outside of the system through a line f.

In the foregoing process flow system, the reflux ratio (flow rate of water fed at the tower top through the line d/ flow rate of water discharged outside through the line e) was set on 1.0, and n-butyl acetate was consecutively supplied to the decanter 4 in an amount equivalent to the amount of the same dissolved in water discharged outside.

After the start of the operation, a pursuit was performed of the concentration of acetic acid collected from the line e. The results are given in Table 1, which also gives the concentration of p-xylene in n-butyl acetate collected from the delivery port of the pump 5.

TABLE 1

| Nos. of continuous operation days | Conc. of acetic acid in water, % | Conc. of p-xylene in n-butyl acetate, % |
| --- | --- | --- |
| 1 | 0.011 | 0.0 |
| 3 | 0.013 | 1.8 |
| 7 | 0.063 | 8.2 |
| 14 | 0.18 | 12.9 |
| 21 | 0.22 | 17.3 |

As is clearly understood from the Table 1, the concentration of the acetic acid in effluent water increased with the lapse of continuous operation days, in other words, the separation efficiency of the azeotropic dehydration deteriorated as the operation continued, and further the concentration of p-xylene in n-butyl acetate gradually increased with the lapse of continuous operation days.

EXAMPLE 1

Figure 2:
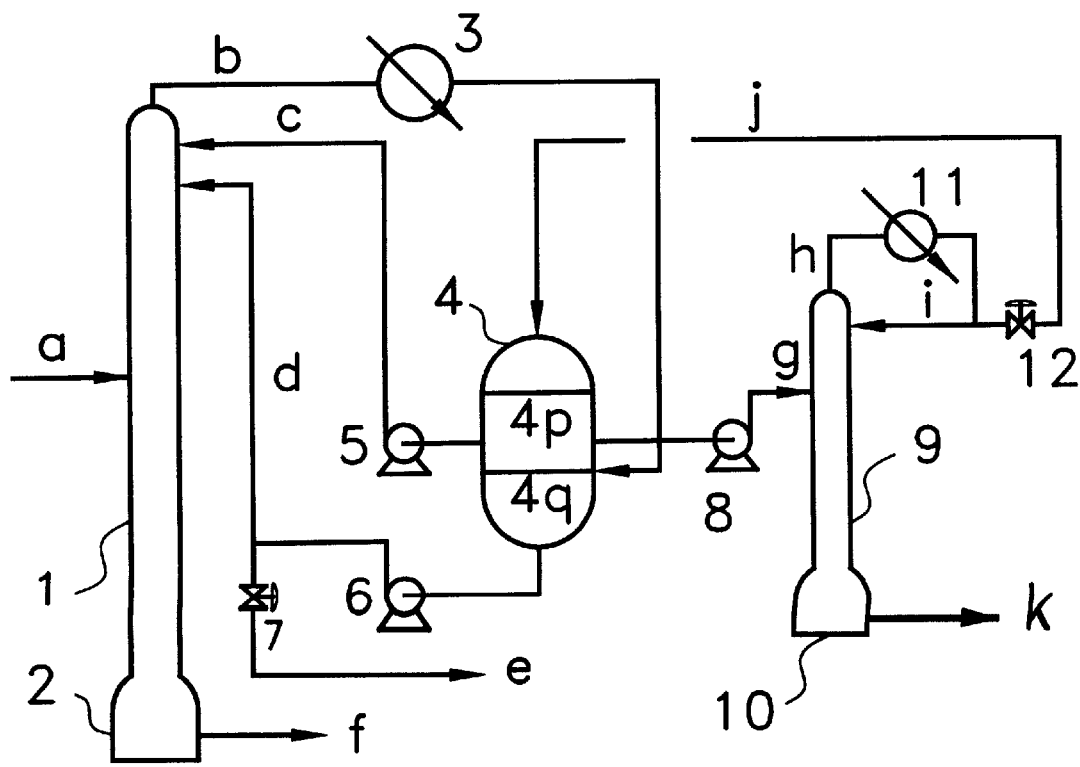
FIG. 2 is a process flow diagram showing a dehydration apparatus for water-containing acetic acid to be employed in working examples, in which the symbols shall have the following designations.

To the apparatus which had been used in Comparative Example 1 was added a refining step as shown in FIG. 2 for removing p-xylene which had been accumulated in n-butyl acetate, and continuous dehydration operation was performed in the same manner as in Comparative Example 1.

There was used as a rectifying tower 9 in FIG. 2, a glass-made distillation tower having 6 tray plates. In the first place, a reboiler 10 was charged with a mixed liquid of p-xylene and n-butyl acetate, and was heated for steaming into the tower. The resultant vapor was passed through a line h, cooled in a condenser 11, and the condensate thus formed was totally refluxed at the top of the tower through a line i. When a stable total-reflux operation was attained, by operating a pump 8, the n-butyl acetate of the upper layer 4p in the decanter 4 was withdrawn in part, and was fed at an intermediate stage of the rectifying tower 9 through a line g. Simultaneously therewith, a valve 12 was opened to return part of the distillate to the decanter 4 through the line j.

Thus, continuous operation was carried out in the same manner as in Comparative Example 1 except that the rectifying step and procedure were incorporated. The reflux ratio (flow rate of distillate returend to the tower through the line i/flow rate of distillate returend to the decanter through the line j) was set on 8, approx. The p-xylene which gathered in the reboiler 10 and contained a small amount of n-butyl acetate was consecutively taken out to the outside of the system through a line k.

After the start of the operation, a pursuit was performed of the concentration of acetic acid collected from the line e. The results are given in Table 2, which also gives the concentration of p-xylene in n-butyl acetate collected from the delivery port of the pump 5.

TABLE 2

| Nos. of continuous operation days | Conc. of acetic acid in water, % | Conc. of p-xylene in n-butyl acetate, % |
| --- | --- | --- |
| 1 | 0.013 | 0.0 |
| 3 | 0.015 | 1.2 |
| 7 | 0.039 | 3.5 |
| 14 | 0.062 | 7.9 |
| 21 | 0.058 | 7.0 |

REFERENCE EXAMPLES 1 to 4

Observations were made of the variation in efficiency of the dehydration tower 1 with the case where p-xylene was mixed in n-butyl acetate.

In the same manner as in Comparative Example 1, the dehydration tower 1 was charged through the line a with water-containing acetic acid consisting of 60 parts of reagent-grade glacial acetic acid and 40 parts of water, while an azeotropic agent was used which was composed of reagent-grade n-butyl acetate incorporated in advance with 0, 5, 10 and 15% of p-xylene (px). At the time when a stable steady-state was attained for the overall system, an analysis was made of the concentrations of acetic acid collected from the line e. The results are given in Table 3.

TABLE 3

| Reference Example | Amount of px added to n-butyl acetate, % | Conc. of acetic acid in water, % |
|---|---|---|
| 1 | 0 | 0.021 |
| 2 | 5 | 0.054 |
| 3 | 10 | 0.15 |
| 4 | 15 | 0.31 |

It can be seen from Table 3 that, as the amount of p-xylene added to n-butyl acetate increases, the efficiency of the dehydration tower 1 decreases, and further the concentration of acetic acid in effluent water increases, and said concentration steeply increases when the amount of p-xylene present in n-butyl acetate exceeds 10% in particular.

COMPARATIVE EXAMPLE 2

The procedure in Comparative Example 1 was repeated except that there was used as the starting material, a reflux liquid of oxidation reaction in a commercially operated production plant for isophthalic acid, said liquid comprising about 65% of acetic acid and the balance mainly of water.

After the start of the operation, pursuit was performed of the concentration of acetic acid collected from the line e. The results are given in Table 4, which also gives the concentration of m-xylene in n-butyl acetate collected from the delivery port of the pump 5.

TABLE 4

| Nos. of continuous operation days | Conc. of acetic acid in water, % | Conc. of m-xylene in n-butyl acetate, % |
|---|---|---|
| 1 | 0.012 | 0.0 |
| 3 | 0.012 | 2.1 |
| 7 | 0.059 | 8.8 |
| 14 | 0.11 | 11.8 |
| 21 | 0.20 | 18.1 |

As clearly understood from the Table 4, the concentration of the acetic acid in effluent water gradually increased with the lapse of continuous operation days, in other words, the separation efficiency of the azeotropic dehydration deteriorated as the operation continued, and further the concentration of the m-xylene in n-butyl acetate increased with the lapse of continuous operation days.

EXAMPLE 2

To the apparatus which had been used in Comparative Example 2 as added a refining step as shown in FIG. 2 for removing m-xylene which had been accumulated in n-butyl acetate, and continuous dehydration operation was performed in the same manner as in Comparative Example 2.

After the start of the operation, pursuit was performed of the concentration of acetic acid collected from the line e. The results are given in Table 5, which also gives the concentration of m-xylene in n-butyl acetate collected from the deliver port of the pump 5.

TABLE 5

| Nos. of continuous operation days | Conc. of acetic acid in water, % | Conc. of m-xylene in n-butyl acetate, % |
|---|---|---|
| 1 | 0.013 | 0.1 |
| 3 | 0.013 | 1.8 |
| 7 | 0.031 | 3.0 |
| 14 | 0.054 | 8.1 |
| 21 | 0.056 | 8.0 |

It can be seen from Table 5 that by removing m-xylene which has been accumulated in n-butyl acetate by using the rectifying power, the concentration of acetic acid in the effluent water is maintained at an almost constant level even after the lapse of over 20 days and likewise, that the concentration of m-xylene in n-butyl acetate is maintained at an almost constant level.

The following is a summary of the comparative examples, working examples and reference examples as described herein before.

(1) When azeotropic dehydration is carried out by feeding, to a dehydration tower, a reflux liquid of oxidation reaction in a commercially operated production plant for an aromatic carboxylic acid using n-butyl acetate as an azeotropic agent, the concentration of the acetic acid in effluent water gradually increases with the lapse of continuous operation days, in other words, the separation efficiency of the azeotropic dehydration deteriorates as the continuous operation days, in other words, the separation efficiency of the azeotropic dehydration deteriorates as the operation continues, and further the concentration of the alkyl-group-substituted aromatic compound in n-butyl acetate increases with the lapse of continuous operation days (refer to Comparative examples 1&2).

(2) The concentration of acetic acid in the effluent water can be maintained at a low level even after the lapse of a number of continuous operation days by adding a step of discharging alkyl-group-substituted aromatic compounds which have been accumulated in n-butyl acetate to the outside of the system and thereby suppressing the concentration of alkyl-group-substituted aromatic compounds in the azeotropic agent to a minimum level (refer to examples 1 & 2).

(3) When the dehydration operation is carried out in such a manner that a mixture of reagent-grade acetic acid and water is fed in a dehydration tower and an alkyl-group-substituted aromatic compound is consecutively added to n-butyl acetate as the azeotropic agent, the concentration of the acetic acid in effluent water increases with an increase in the amount of the alkyl-group-substituted aromatic compound which is consecutively added to n-butyl acetate, and consequently the separation efficiency of the azeotropic dehydration is deteriorated (refer to Reference Examples 1 to 4).

What is claimed is:

1. A process for producing an aromatic carboxylic acid which comprises subjecting an alkyl-group-substituted aromatic compound to a liquid-phase oxidation with molecular oxygen in acetic acid as a solvent in the presence of a catalyst in an oxidation reactor;

producing water-containing acetic acid by cooling and condensing an exhaust gas from the oxidation reactor, or by evaporating the resultant oxidation reaction mother liquor from the oxidation reactor after separating the objective aromatic carboxylic acid from the oxidation reaction mother liquid;

dehydrating the resultant water-containing acetic acid by an azeotropic distillation in an azeotropic distillation dehydration tower, feeding an entrainer to a top portion of the azeotropic distillation tower to suppress the concentration of the alkyl-group substituted aromatic compound in the entrainer to a concentration of at most 10% by weight; and recycling to the oxidation reaction the resultant dehydrated acetic acid as the solvent.

2. The process for producing an aromatic carboxylic acid according to claim 1, wherein the alkyl-group-substituted aromatic compound as a starting material is selected from the group consisting of p-xylene and m-xylene, and the objective aromatic carboxylic acid is selected from the group consisting of terephthalic acid and isophthalic acid.

3. The process for producing an aromatic carboxylic acid according to claim 1, wherein the entrainer is n-butyl acetate.

4. The process for producing an aromatic carboxylic acid according to claim 1, wherein the water-containing acetic acid is fed to the azeotropic distillation dehydration tower at an intermediate stage thereof; an azeotropic mixture distilled away through the top portion of said azeotropic distillation dehydration tower is cooled and condensed; the resultant condensate is introduced to a decanter to separate the entrainer from water; at least part of the entrainer which is separated in said decanter is distilled to remove the alkyl-group-substituted aromatic compound contained in said entrainer, and thereafter the resultant refined entrainer is fed to said azeotropic distillation dehydration tower at the top portion thereof.

5. The process for producing an aromatic carboxylic acid according to claim 1, wherein the catalyst comprises a transition metal compound selected from the group consisting of manganese, cobalt, iron, chromium and nickel; and the liquid phase oxidation is carried out at a temperature of 120 to 220° C.

6. The process for producing an aromatic carboxylic acid according to claim 1, wherein the entrainer is selected from the group consisting of butyl formate, amyl formate, n-butyl acetate, isobutyl acetate, alkyl acetate, n-propyl propionate, isopropyl propionate, n-butyl propionate, iso-butyl propionate, dichloromethyl ether, ethylisoamyl ether, amyl chloride, ethylene dichloride, acetone chloride, ethyl propyl ketone and toluene.

7. The process for producing an aromatic carboxylic acid according to claim 6, wherein the alkyl-group-substituted aromatic compound is selected from the group consisting of p-xylene and m-xylene; and the aromatic carboxylic acid is selected from the group consisting of terephthalic acid and isophthalic acid.

8. The process for producing an aromatic carboxylic acid according claim 7, wherein the entrainer is n-butyl acetate.

9. The process for producing an aromatic carboxylic acid according to claim 8, wherein the alkyl-group substituted aromatic compound is p-xylene.

10. The process for producing an aromatic carboxylic acid according to claim 8, wherein the alkyl-group substituted aromatic compound is m-xylene.

* * * * *